United States Patent
Schaeffer (10) Patent No.: US 9,877,711 B2
(45) Date of Patent: Jan. 30, 2018

(54) EXPANDABLE VASCULAR CLOSURE PLUG

(71) Applicant: Cook Medical Technologies LLC, Bloomington, IN (US)

(72) Inventor: Darin G. Schaeffer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 646 days.

(21) Appl. No.: 14/476,803

(22) Filed: Sep. 4, 2014

(65) Prior Publication Data

US 2015/0065977 A1 Mar. 5, 2015

Related U.S. Application Data

(60) Provisional application No. 61/873,860, filed on Sep. 5, 2013.

(51) Int. Cl.
*A61B 17/00* (2006.01)
*A61L 31/14* (2006.01)
*A61L 27/36* (2006.01)

(52) U.S. Cl.
CPC ...... *A61B 17/0057* (2013.01); *A61L 27/3633* (2013.01); *A61L 31/146* (2013.01); *A61B 2017/00654* (2013.01); *A61B 2017/00898* (2013.01); *A61L 2400/04* (2013.01)

(58) Field of Classification Search
CPC ...... A61B 17/0057; A61B 2017/00898; A61B 2017/00862; A61B 17/10; A61L 27/3633; A61L 31/146; A61L 2400/04; A61F 13/2002; A61M 1/3655; A61M 1/0026; A61M 2025/068; A61M 25/04; A61M 25/1011; A61M 2025/0063; A61M 2025/0004

USPC .......................................................... 606/213
See application file for complete search history.

(56) References Cited

U.S. PATENT DOCUMENTS

| | | | |
|---|---|---|---|
| 4,890,612 A | 1/1990 | Kensey | |
| 5,370,660 A | 12/1994 | Weinstein et al. | |
| 6,699,261 B1 | 3/2004 | Cates et al. | |
| 2002/0055780 A1* | 5/2002 | Sklar | A61F 2/0811 623/13.12 |
| 2010/0198254 A1 | 8/2010 | Schaeffer | |
| 2010/0249830 A1 | 9/2010 | Nelson | |

(Continued)

OTHER PUBLICATIONS

Ethicon, Inc.'s Wound Closure Manual, edited by Dr. Dunn, 2005, <http://www.uphs.upenn.edu/surgery/Education/facilities/measey/Wound_Closure_Manual.pdf>.*

*Primary Examiner* — Tatyana Zalukaeva
*Assistant Examiner* — Gabriella Burnette
(74) *Attorney, Agent, or Firm* — Woodard, Emhardt, Moriarty, McNett & Henry LLP (57) ABSTRACT

Described are devices useful for providing hemostasis at a vascular access site, and related methods. Such devices can include first and second implant members cooperable when forced together to expand the first implant member in a tissue tract at the site. Such devices can also include an anchor member and a tether attached thereto. The anchor member can be deployed distally to the first implant member, within a vessel, and the tether can be tensioned to apply counterforce to the first implant member as the second implant member is forced into cooperative contact to expand the first implant member.

19 Claims, 6 Drawing Sheets

(56) References Cited

U.S. PATENT DOCUMENTS

2011/0301619 A1* 12/2011 Walters .............. A61B 17/0057
606/144

* cited by examiner

EXPANDABLE VASCULAR CLOSURE PLUG

BACKGROUND

The present disclosure relates generally to medical devices and methods, and in certain aspects to methods and devices for retaining a plug or similar device in place to maintain hemostasis after a procedure that disrupts a vascular vessel, and in particular embodiments after a percutaneous vascular intervention procedure.

Vascular disease is one of the leading causes of deaths today. In many instances, such a disease requires the insertion of a medical device into the lumen of a vascular vessel. Depending on the size of the opening required to insert the medical device into the vessel, and depending on the type of vessel (i.e., vein vs. artery), these openings can cause a variety of complications, including access site bleeding and/or infection. Many types of arteriotomy closure devices exist, and they can be constructed of a variety of materials and can be used in a variety of different ways to achieve hemostasis. For example, in a percutaneous coronary intervention, a device is inserted into the femoral artery. When this device is withdrawn from the artery, methods must be taken to control the exit of blood from the artery or the patient would require a blood transfusion.

Historically, the most common approach to control this problem involved the practitioner simply applying manual compression to the access site until the wound has had a chance to heal itself sufficiently. More recently, a puncture closing device, such as a hemostatic patch or plug, is inserted into the opening of the vessel. The hemostatic plug is typically formed of a bioresorbable material such that it can degrade in vivo and its removal from the patient is unnecessary. The plug stays in place long enough to control bleeding and then degrades over time. The problem with this technique is that the patch or plug can become dislodged from the vessel opening, thereby requiring further action to control the bleeding.

Although vascular closure devices exist, there remain needs for improved and/or alternative devices for maintaining hemostasis, as well as methods for making and using the same.

SUMMARY

In certain of its aspects, the present disclosure features unique devices for providing and maintaining hemostasis in which multiple pieces or portions of material cooperate to expand and secure a plugging body at a treatment site. In one embodiment, provided is a device for providing hemostasis at a surgical site in a patient, where the surgical site includes a puncture in a vascular vessel and a tissue tract extending from the skin of the patient to the puncture. The device includes a delivery cannula having at least a portion advanceable into the tissue tract and through the puncture. A first implant member is provided for implantation in the tissue tract, the first implant member received in the delivery cannula. A second implant member is provided for implantation in the tissue tract, the second implant member also received in the delivery cannula. The first and second implant members, preferably provided as separate or non-integral members, are sized and configured such that movement of at least a portion of the second implant member against the first implant member causes the first implant member to expand. The device can also include an anchor member received in the delivery cannula, the anchor member configured to reside and anchor within the vessel upon deployment from the delivery cannula and contact an inner surface of the vessel. A tether can be connected to the anchor member, the tether configured to extend through the puncture and tissue tract when the anchor member is received within the vessel. When the anchor member is provided, the first and second implant members can be received in the delivery cannula proximal to the anchor member. In additional embodiments, a pusher is received in the delivery cannula for imparting a pushing force against the second implant member. The first and second implant members can be sized and configured such that the movement noted above causing expansion of the first implant member also causes overlap of the first and second implant members with one another, which overlap can be an original amount of overlap from a non-overlapped condition, or an additional amount of overlap from a partially-overlapped condition. The first and second implant members can also be sized and configured such that the above-noted movement causes the first and second implant members to frictionally couple to one another. The first implant member can define a lumen and the second implant member can define at least a portion receivable within the lumen of the first implant member so as to expand the first implant member. In embodiments described herein, at least a portion of the second implant member can be received in the delivery cannula proximal to the first implant member. In certain aspects, the first implant member has a lumen extending at least partially along a length of the first implant member, the second implant member has at least a portion received outside of and movable into the lumen of the first implant member upon said movement; and the anchor member, tether and pusher are provided and so constructed and arranged that the tether can be tensioned to cause the anchor member to provide proximally-directed counterforce to the first and/or second implant member while the pusher is advanced distally to cause the above-noted movement that expands the first implant member.

In another embodiment, the present disclosure provides a device for providing hemostasis at a surgical site in a patient, where the surgical site includes a puncture in a vascular vessel and a tissue tract extending from the skin of the patient to the puncture. The device includes a first implant member sized for receipt in the tissue tract, the first implant member having a proximal end and a distal end, and a second implant member sized for receipt in the tissue tract, the second implant member having a proximal end and a distal end. The first and second implant members, preferably provided as separate or non-integral members, are sized and configured such that movement of at least a portion of the second implant member against the first implant member causes frictional coupling of the first and second implant members and urges the first implant member to expand. The device also includes at least one force-transmitting member for causing said movement. The at least one force transmitting member can include a pusher arranged to apply distally-directed force to the second implant member, or an anchor member residing distal of the distal end of the first implant member and a tether connected to the anchor member, the anchor member and tether arranged to apply proximally-directed force to the first implant member, or both such pusher and anchor member-tether combination. The first implant member can have an opening at the proximal end of the first implant member and an internal lumen communicating with the opening and extending at least partially along a length of the first implant body. The second implant member can have at least a portion residing proximal of the opening at the proximal end of the first implant member, with such portion being movable into the lumen of the first implant member during the movement of at least a portion of the second implant member against the first implant member that causes frictional coupling of the first and second implant members and urges the first implant member to expand. The second implant member can be more resistant to compression than the first implant member.

In another embodiment, the present disclosure provides a method for providing hemostasis at a surgical site in a patient, where the surgical site includes a puncture in a vascular vessel and a tissue tract extending from the skin of the patient to the puncture. The method includes deploying a first implant member and a second implant member in the tissue tract, and moving the second implant member against the first implant member so as to cause expansion of the first implant member in the tissue tract. The method can also include deploying an anchor member through the tissue tract, through the puncture site and into the vessel, the anchor member having attached thereto a tether extending out of the puncture site, through the tissue tract and external of the patient. The method can further include applying proximally-directed force to the first implant member with the tether during the movement of the second implant member against the first implant member. In these methods, any and all devices and components thereof (e.g., specific size, shape or functional characteristics of the first and second implant member) as described above and hereinafter, or any additional method steps as described above or hereinafter, can be used in providing the hemostasis.

The present disclosure also provides methods for the manufacture of devices and apparatuses as described herein.

Additional aspects as well as features and advantages of the presenting disclosure will be apparent to those of ordinary skill in the art from the descriptions herein.

DETAILED DESCRIPTION

For the purposes of promoting an understanding of aspects of the invention, reference will now be made to certain embodiments and specific language will be used to describe the same. It will nevertheless be understood that no limitation of the scope of the invention is thereby intended. Any alterations and further modifications in the illustrative devices or methods described herein, and further applications of the principles of the invention as illustrated herein, are contemplated as would normally occur to one skilled in the art to which the invention pertains.

As disclosed above, in certain aspects, the present disclosure provides unique products and methods for providing hemostasis in a patient. In some forms, implantable devices useful in the present disclosure include an expandable member having a lumen extending at least a portion of the way therethrough. The lumen of the expandable member is sized and shaped to receive an expander. In certain embodiments, the device can further include an anchor member configured for placement distal to the expandable member. In some preferred forms, all or part of the expandable member, expander and/or anchor member will comprise a remodelable material such that the patient's tissue can remodel the implant to enhance and promote hemostasis at the surgery site.

Figure 1:
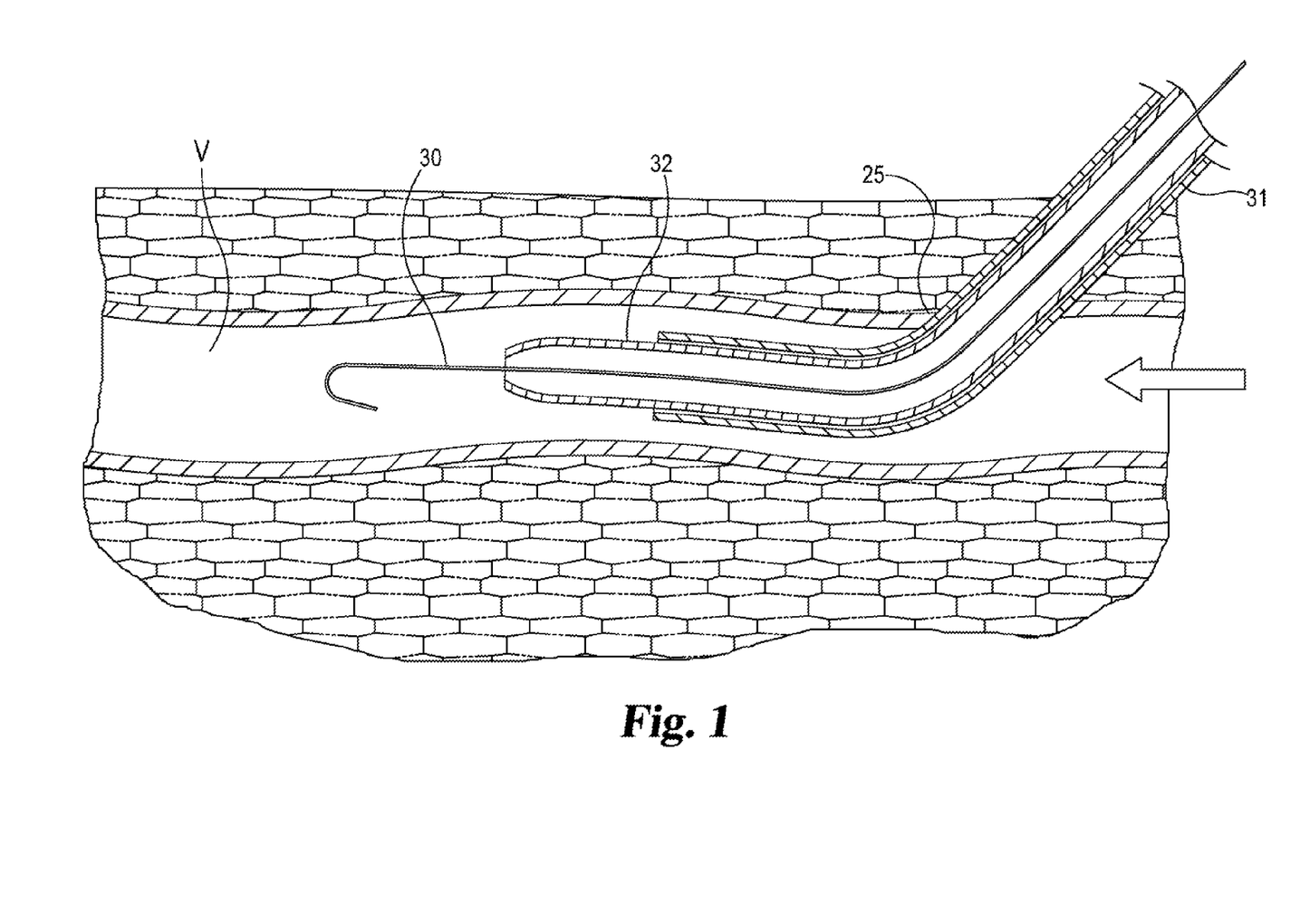
FIG. 1 provides a perspective view of a delivery sheath for use in delivering a medical device as described herein.

Turning more specifically now to FIG. 1, shown is an enlarged view of a bodily vessel "V". In an illustrative deployment procedure, percutaneous access to the vessel can be achieved at location 25 using the Seldinger or any other suitable technique. For instance, an access needle (not shown) can be passed through the skin to access the vessel, and a wire guide 30 or other suitable elongate guiding member can be passed through the access needle and into the vessel. In conjunction with or as part of an inventive method, wire guide 30 can be used for any number of conventional procedures including catheterization and imaging procedures. After any such procedures are performed, the wire guide 30 can be removed or in other embodiments can be used to assist in the delivery of devices and materials as described herein.

With continuing reference to FIG. 1, a procedural sheath 31 can be placed at a suitable location in the vessel using a flexible guide catheter 32, or, alternatively, a suitable dilator or dilator tip mounted on the guide catheter. In placing or inserting the sheath 31 in the vessel, the guide catheter 32 can be first received over the wire guide 30 and then pushed into the vessel, where it follows along the wire guide 30 to a location within the vessel. Next, the sheath 31 can be received over the guide catheter 32, pushed into the vessel, and follow the guide catheter 32 to a suitable location in the vessel. Alternatively, the sheath 31 and guide catheter 32 can be placed within the vessel, with the guide catheter 32 leading the sheath 31, and both can be pushed along the wire guide 30 until the sheath 31 is in a suitable location. Still alternatively, a steerable catheter can be used in conjunction with a sheath, thereby negating the need for a wire guide. Accordingly, inventive products and methods can be adapted for use in conjunction with procedures that employ any number of sheaths, catheters, wires and/or other endoluminally advanceable devices.

Endoluminally advanceable devices useful in the present disclosure (e.g., guidewires, catheters, etc.) can be shaped and configured in a variety of manners. A device might be constructed to traverse a body passageway without buckling or kinking or causing unacceptable damage to soft tissues defining the passageway. In some forms, the distal end of a device, or a portion thereof, will be particularly configured to avoid substantially cutting or tearing surrounding soft tissues or otherwise enhance its travel through body passageways. For example, a device distal end can include a tapered portion and/or have a dome-shaped or otherwise rounded tip. Selected portions of a device (e.g., the distal end), might be rigid, malleable, semi-flexible, or flexible. In certain embodiments, an endoluminally advanceable device is particularly adapted for moving through and into body passages that angulate sharply or curve abruptly. In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner. In some forms, a device will be somewhat rigid in terms of column strength, yet will be equipped with one or more reliefs, indentations, thinner portions, or other similar adaptations along the device to provide some lateral flexibility to the device. Additionally or alternatively, a device may incorporate a mechanism of some sort that enables an operator to steer or otherwise navigate the device through a tortuous body passageway. These and other adaptations for facilitating advancement of a device through a body passageway will be recognized by those skilled in the art, and therefore, are encompassed by the present disclosure. In some aspects, components for visualizing and/or irrigating a body passageway can be received within an endoluminally advanceable device lumen as discussed herein.

Sheaths, dilators, endoluminal deployment devices, such as pushers, wire guides and needles used in the present disclosure can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook Medical Incorporated). Dilators and pushers can be made from conventional dilator/catheter/pusher type materials such as polyethylene, polyamide, polyurethane or vinyl, stainless steel, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

Figure 2:
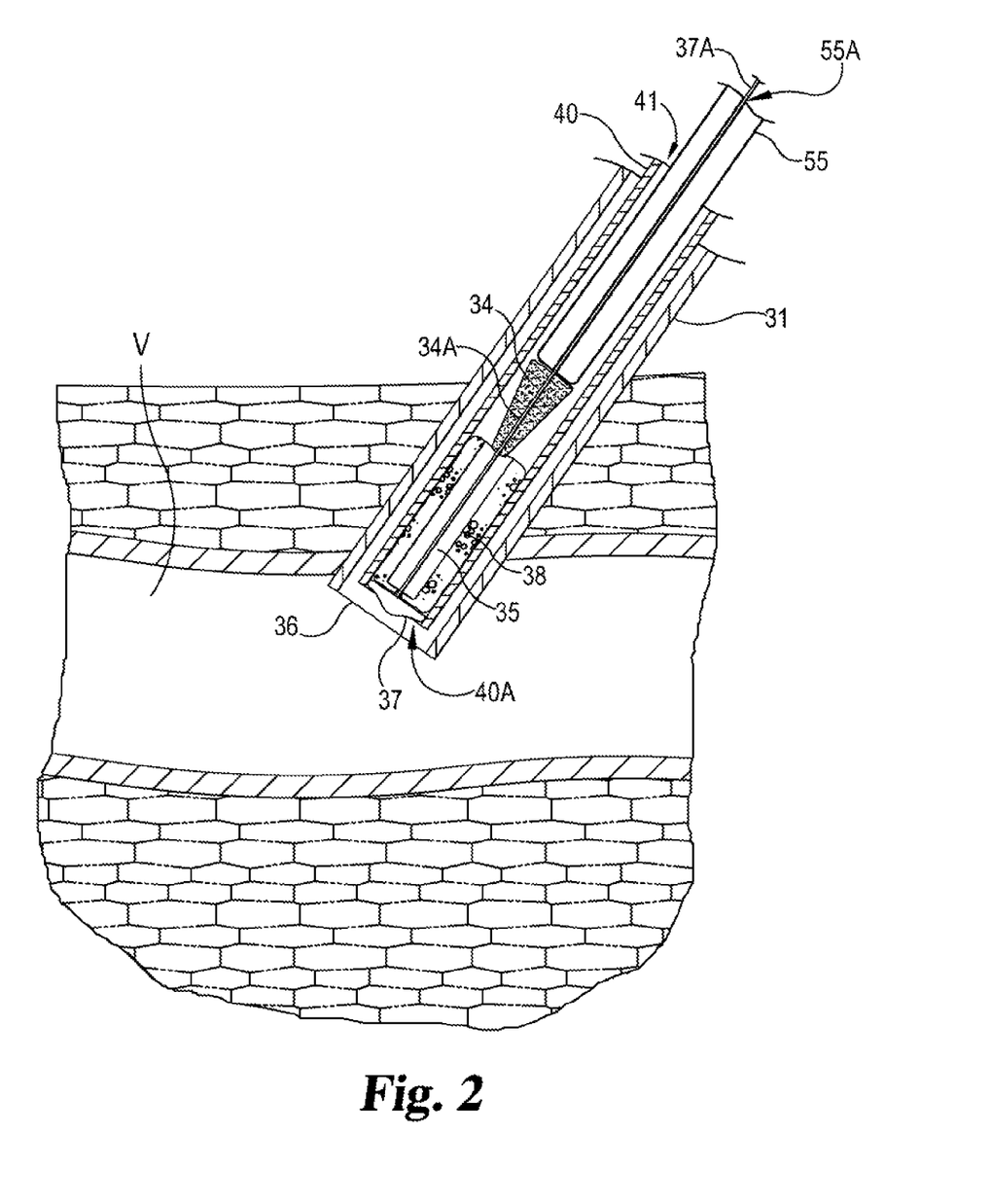
FIG. 2 provides a perspective view of a medical device as described herein further including an implant prior to deployment.

With further reference to FIG. 1, potentially after the completion of an interventional procedure, guide catheter 32 and wire guide 30 can be removed to leave sheath 31 in the vessel. Removal of sheath 31 would cause bleeding from location 25. Referring now to FIG. 2, shown is an embodiment of the present disclosure designed to prevent or reduce such bleeding. A cannula or delivery catheter 40 is shown inserted into sheath 31 and advanced therethrough toward the distal end opening 36 of the sheath. Optionally, wire guide 30 can be left in the sheath, and other components such as delivery catheter 40 can be threaded over the wire and advanced to a desired location. Delivery catheter 40 includes within its lumen 41 a first implant member such as an expandable member 38 having lumen 35, and a second implant member such as an expander 34. These components can be inserted in the lumen 41 of delivery catheter 40 either before or after delivery catheter 40 is inserted into sheath 31. The second implant member such as expander 34 can have a tapered distal end as shown to facilitate its advancement into the lumen of expandable member 38. This advancement can cause frictional engagement or coupling between the first and second implant members (e.g., expander 34 and expandable member 38).

While specific embodiments of the first and second implant members are shown and described in connection with expander 34 and expandable member 38, it will be understood that other embodiments are contemplated within the present disclosure, including for example embodiments in which either or both implant members may include a lumen, and/or the position of either or both components, proximal-to-distal, may be reversed. These and other arrangements, in which the first and second implant members cooperate to form a potentially overlapped and potentially frictionally coupled implant structure having a larger outer diameter or dimension than either implant member considered individually, are contemplated as within the present disclosure. As well, while the use of first and second discrete or separate implant members is described herein, it will be understood that a single integral or connected structure could be used to provide the first and second implant members, or that still additional implant members (e.g., for receipt within the tissue tract adjacent the vessel puncture) could also be used. Any such additional implant members can optionally cooperate with the first and second implant members to engage and provide an even larger overall diameter to the combined implant members. These and other variations will be within the purview of those skilled in the pertinent field upon reviewing the descriptions herein.

Continuing with FIG. 2, lumen 41 of delivery catheter 40 communicates with distal opening 36. Expandable member 38 is removably positioned in catheter lumen 41 and is deployable therefrom through the distal opening 40A for implantation. In this specific illustrative embodiment, expandable member 38 includes a lumen 35 extending therethrough for receiving the expander 34. In one preferred embodiment, the expandable member 38 comprises a compressible material such as an extracellular matrix (ECM) sponge material, although expandable member can be formed with a variety of sponge and non-sponge materials. A force transmitting member such as an elongate pusher 55 can also be received in the catheter lumen 41, and is translatable through the lumen 41 for urging the expander 34 into the lumen of the expandable member 38 and/or for urging the expandable member 38 from the catheter lumen 41.

An anchor member 37 can be included at the distal end of expandable member 38. Anchor member 37 can be a T-bar, a cap (e.g., foldable or compressible for delivery), or any other suitable anchor structure. Anchor member 37 can be formed of any of the materials described herein as long as it can be oriented, folded, wrapped, compressed or otherwise manipulated to fit within a sheath and/or delivery catheter and thereafter deploy to provide an anchor (e.g., within the vessel). Anchor member 37 is constructed and arranged such that upon deployment within the vessel, the anchor member extends to a configuration having a cross-sectional dimension that is greater than the cross-sectional dimension of the opening in the vessel and/or of the first or second implant members. In this way, anchor member resists withdrawal back through the opening in the vessel and into the tissue tract. Anchor member 37, when present, can be held in association with expandable member 38 in any suitable fashion, for example by being connected to expandable member and/or to expander 34 by one or more sutures.

In some embodiments, anchor member 37 sealingly engages with an inner surface of the vessel so as to form a fluid-tight seal around the opening in the vessel and resist and/or prevent the flow of fluid from vessel into the tissue tract. For example, the anchor member can have a proximally facing surface (e.g., a surface that faces the first and second implant members) that upon a withdrawing motion of the anchor member contacts the inner surface of the patient's vessel. In several embodiments, anchor member 37 presents a smooth, non-thrombogenic surface that faces towards the lumen of the vessel. Additionally, in some instances, only the thickness of anchor member 37 extends into the lumen of the vessel. For example, the anchor member 37 can comprise a disc having a thickness and a width, the width being greater than the thickness, and a distal surface of anchor member 37 being spaced away from the vessel wall the thickness of anchor member 37 when anchor member 37 is positioned in a sealing configuration across and around the opening in the vessel. In many instances, after the disclosed device is positioned within the body of a patient, surfaces of anchor member 37 are exposed to the lumen of the vessel and the implant members are positioned within the tissue tract.

In the embodiment shown, anchor member 37 is connected to a flexible tether such as a tether 37A that extends through lumen 55A of pusher 55, lumen 34A of expander 34, and lumen 35 of expandable member 38. Tether 37A can also extend along an outermost surface of portions of pusher 55, expander 34 and/or expandable member 38. Tension on tether 37A, for example imparted by a user pulling on tether 37A, can be used to retain anchor member 37 in association with a wall of the vessel and/or with the distal end of expandable member 38 and potentially in contact therewith. In FIG. 2, the distal end of delivery catheter 40 is shown in a position advanced into the blood vessel. From this position, sheath 31 can be withdrawn and/or catheter 40 can be advanced, and anchor member 37 can be deployed out of the distal end opening 36 and into the vessel, using counterforce applied by pusher 55 as delivery catheter 40 is withdrawn and/or by holding the position of delivery catheter 40 and advancing pusher 55.

In this regard, in the illustrated embodiment, force applied to pusher 55 is transmitted to expander 34 by contact of the pusher 55 distal end with the expander 34 proximal end. This force is in turn transmitted to expandable member 38 through contact of expander 34 with expandable member 38, and in turn the force is transmitted to anchor member 37 through contact of expandable member 38 with anchor member 37. The contact of expander 34 with expandable member 38 to transmit this force as necessary to deploy anchor member 37, expandable member 38 and expander 34 from the distal end opening 36, may or may not cause expander 34 to enter lumen 35 of expandable member 38, partially or fully. In preferred forms, during this force and contact for deployment from delivery catheter 40, expander 34 will not advance into lumen 35, or only a portion of expander 34 will advance into lumen 35. The dimensions, shape and materials of construction for these components can be varied to achieve these functions.

Figure 3:
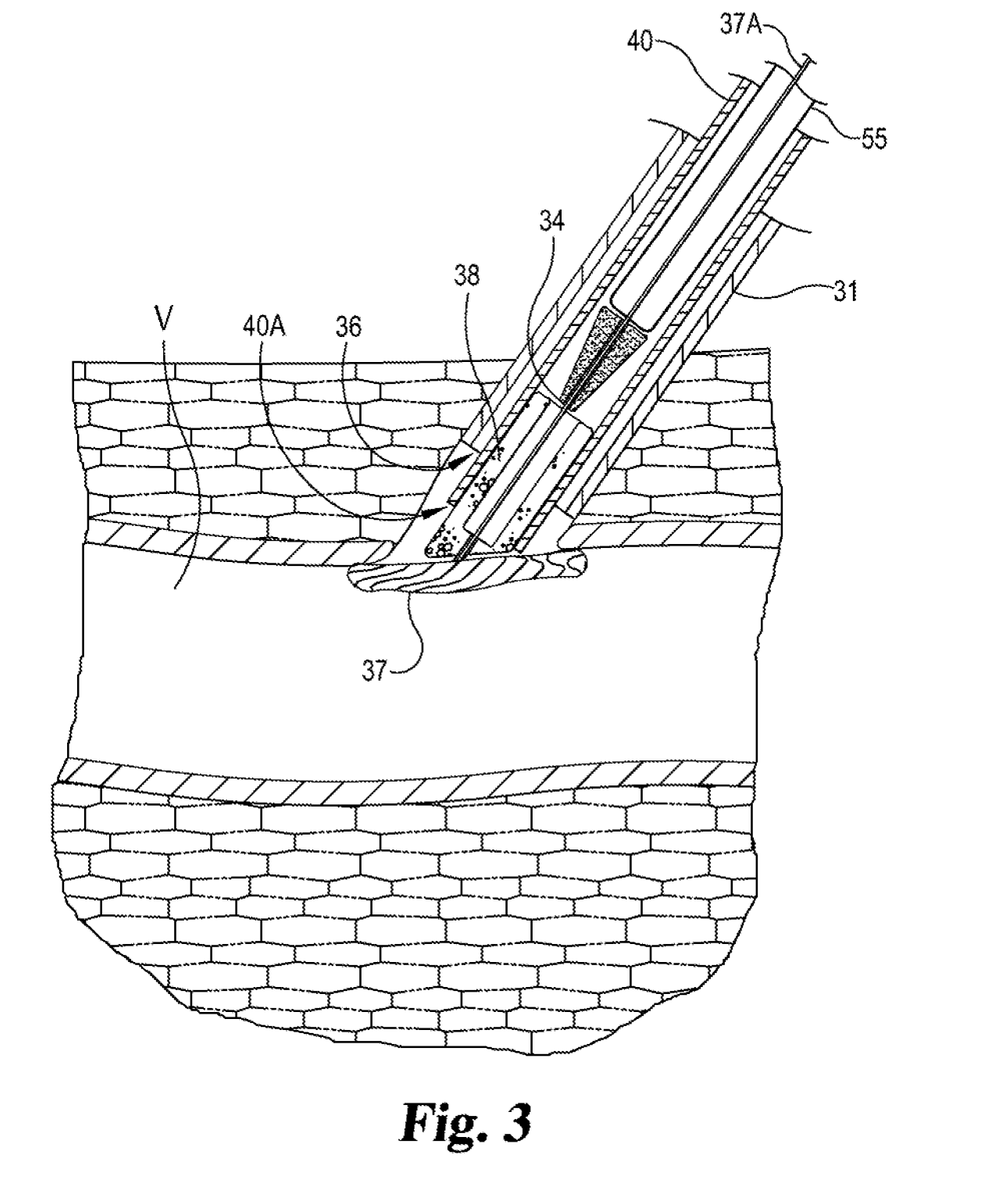
FIG. 3 provides a perspective view of the medical device of FIG. 2 during deployment wherein the anchor member is in an unfolded configuration.

Turning now to FIG. 3, shown is the assembly of FIG. 2 with the anchor member 37 deployed in the vessel and the tether 37A pulled in a proximal direction so as to position a proximal facing surface of the anchor member 37 against the inner surface of the wall of the vessel. Additionally, the sheath 31 and delivery catheter 40 are withdrawn from the vessel and positioned in the tissue access tract adjacent the vessel wall. Expandable member 38 is shown partially deployed from distal end opening 40A of delivery catheter 40.

Figure 4:
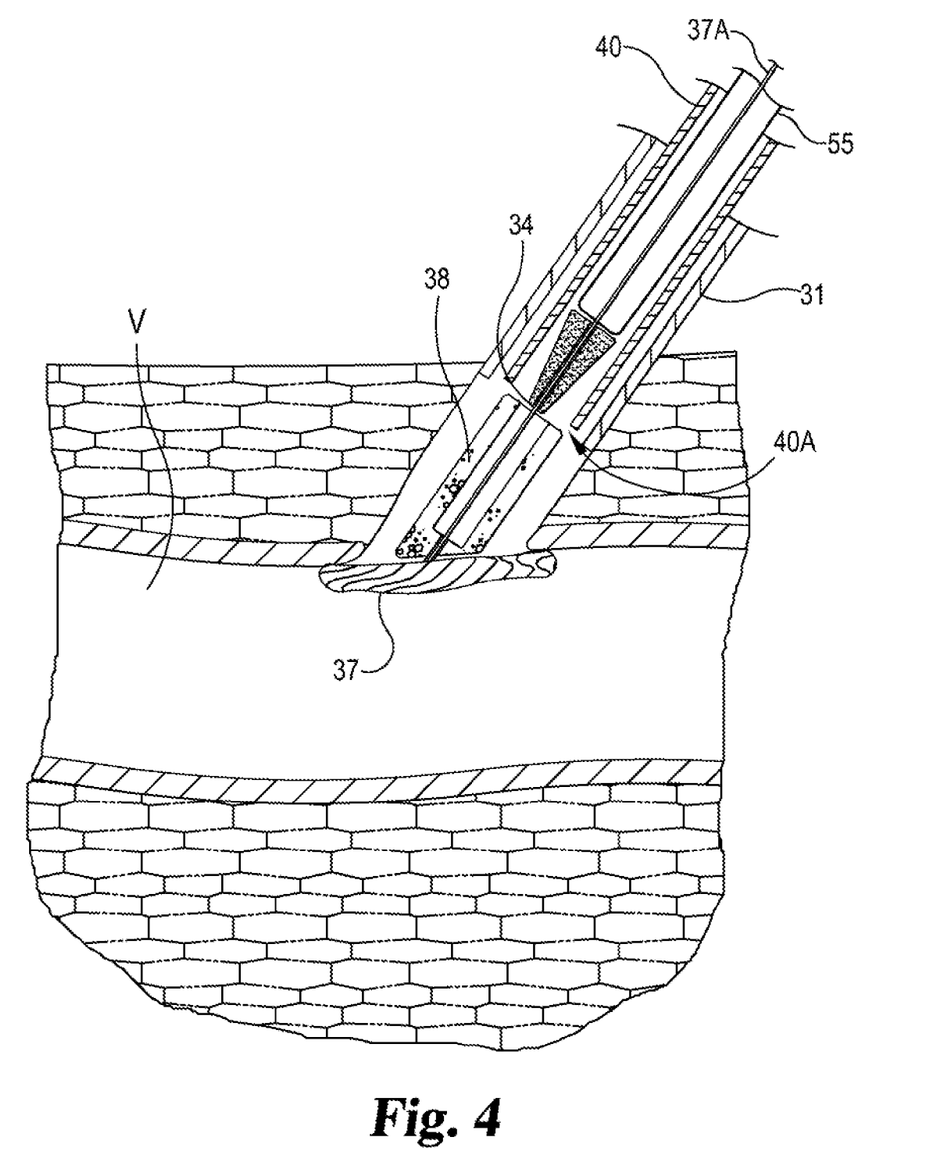
FIG. 4 provides a perspective view of the medical device of FIG. 2 during deployment wherein the delivery catheter has been pulled back to expose the implant.

FIG. 4 illustrates a delivery stage in which expandable member 38 has exited distal end opening 40A of delivery catheter 40, with sheath 31 remaining partially inserted in the tissue tract. In one mode of operation, from this position, tether 37A can be pulled in a proximal direction to urge anchor member 37 against the inner vessel wall and to provide counter force while pusher 55 is advanced in a distal direction to drive the expander 34 into lumen 35 of expandable member 38. In this way, tether 37A exerts a force on anchor member 37 in a proximal direction so as to hold expandable member 38 in place while pusher 55 forces expander 34 into expandable member 38. Because expander 34 has at least a portion that has a cross-sectional dimension greater than lumen 35, advancement of expander 34 into lumen 35 causes the expandable member 38 to expand to have a larger outer cross-sectional dimension, and frictionally couples the expander 34 and expandable member 38. This, optionally in conjunction with a liquid-swellable nature of expandable member 38 and/or expander 34, facilitates anchoring the combined plug assembly of expander 34/expandable member 38 in the tissue tract and/or sealing the opening in the vessel. When a liquid-swellable material (e.g., a wettable sponge or foam or expandable collagenous material such as small intestinal submucosa) is used in the expander 34 and/or expandable member 38, the presence of liquid in the implant region, e.g., patient blood, injected saline, etc., can provide for part of the expansion during or after deployment of the device components.

Figure 5:
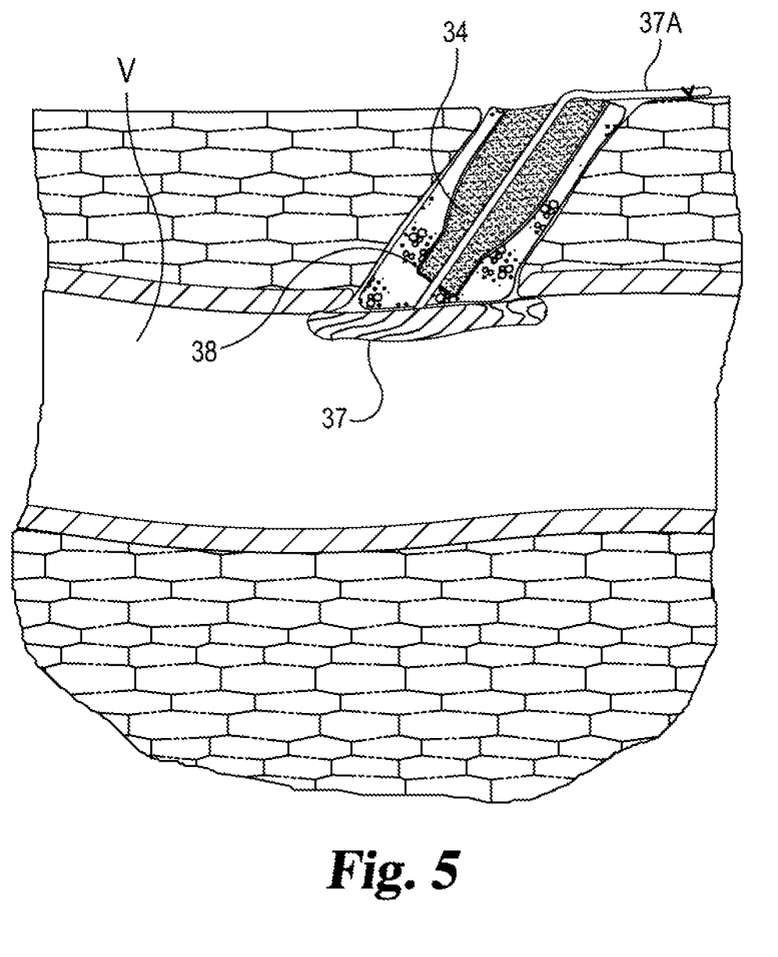
FIG. 5 provides a perspective view of the medical device of FIG. 2 after deployment.

Referring now to FIG. 5, after deployment of the plug components to remain implanted, sheath 31, delivery catheter 40 and pusher 55 can be completely withdrawn, and tether 37A can optionally be secured under tension, e.g., to the skin of the patient adjacent the tissue tract (designated "X" in FIG. 5) or another external device.

Figure 6:
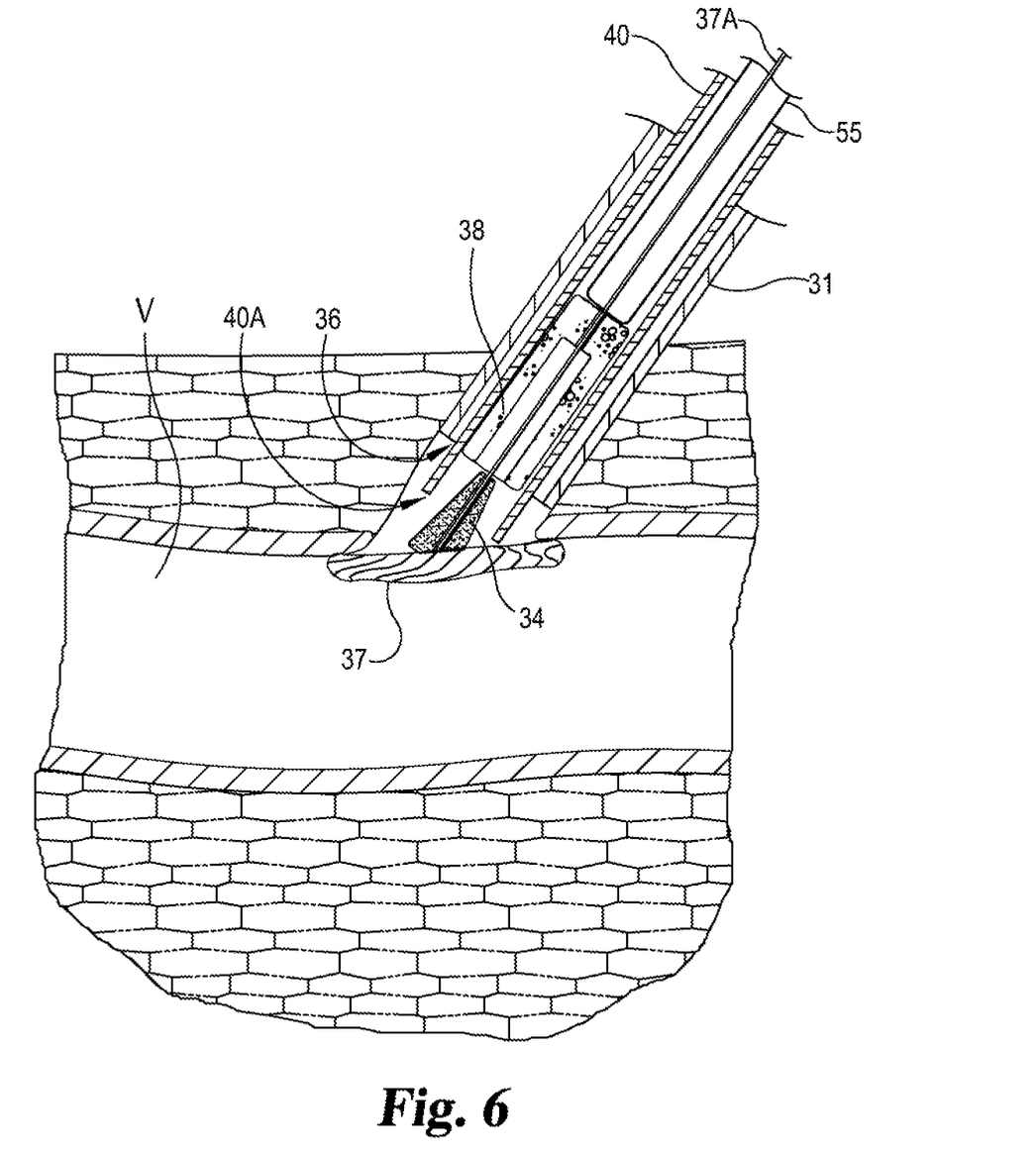
FIG. 6 provides a perspective view of another medical device arrangement during deployment.

FIG. 6 illustrates another arrangement of a medical device in which expander 34 is positioned distally of expandable member 38. In this arrangement, as the two members 34 and 38 are forced against each other (e.g., by pusher 55 pushing on expandable member 38 and anchor member 37 pushing on expander 34), expandable member 38 moves in a distal direction within the tissue tract so as to overlap portions of the expander 34 and/or cause portions of the expander 34 and expandable member 38 to frictionally couple to one another.

The first and second implant members may have a variety of shapes and sizes as will be appreciated by those of ordinary skill in the art. For example, the first implant member may have a hollow-cylindrical shape. Similarly, the second implant member may have a conical, frusto conical, pyramid, wedge, and/or tapered shape. Preferably, the cross-sectional shape of the lumen of the first implant member (i.e., the expandable member) corresponds to the cross-sectional shape of the second implant member (i.e., the expander). For example, in some embodiments the lumen of the first implant member has a cross-sectional shape (e.g., circular) and the end portion of the second implant member that extends into the lumen of the first implant member also has a matching cross-sectional shape. It should be appreciated that while the enclosed drawings illustrate the lumen of the first implant member having a substantial constant cross-sectional dimension (e.g., diameter) prior to the second implant member being inserted therein, any of the embodiments described herein may be arranged with the lumen of the first implant member having tapered or sloping wall portions so that insertion of a constant cross-sectional dimension second implant member or a second implant member having a taper will expand the first implant member.

In other features, sheath 31 and/or delivery catheter 40 can include an optional radiopaque component proximate to its distal end. As is known, the distal ends, or any desirable segment or portion, of the catheters, sheaths, dilators, wires or other components, such as occlusive devices, used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification. As well, distal and/or proximal ends and/or other locations on an expandable member and/or anchor member may include markers for non-invasive imaging, including imageable materials such as those discussed above as well as substances that can be incorporated into occluding materials, e.g., radiopaque elements such as but not limited to a radiopaque coating, attached radiopaque object, or integrated radiopaque substance. Any suitable radiopaque substance, including but not limited to, tantalum such as tantalum powder, can be incorporated into a medical product of the present disclosure. Other radiopaque materials comprise bismuth, iodine, and barium, as well as other suitable markers.

Turning now to a discussion of implant materials useful in preparing expandable member 38 or any other first implant member herein, expander 34 or any other second implant member herein, and/or anchor member 37 as described herein, illustrative such materials can include any suitable biocompatible material. Generally, the materials may include synthetic materials or reconstituted or naturally-derived collagenous materials. Thus, inventive devices can utilize one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, inventive devices can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Biocompatible materials that are at least bioresorbable will provide advantage in certain embodiments of the present disclosure, with materials that are bioremodelable and promote cellular invasion and ingrowth providing particular advantage. Illustratively, remodelable materials may be used in this context to promote cellular growth within the expandable member to promote hemostasis.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more native growth factors such as basic fibroblast growth factor (FGF-2), transforming growth factor beta (TGF-beta), epidermal growth factor (EGF), and/or platelet derived growth factor (PDGF). As well, submucosa or other ECM used in the present disclosure may include other biological materials such as heparin, heparin sulfate, hyaluronic acid, fibronectin and the like. Thus, generally speaking, the submucosa or other ECM material may include a native bioactive component that induces, directly or indirectly, a cellular response such as a change in cell morphology, proliferation, growth, protein or gene expression.

Submucosa or other ECM materials of the present disclosure can be derived from any suitable organ or other tissue source, usually sources containing connective tissues. The ECM materials processed for use in the present disclosure will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the present disclosure will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the present disclosure.

The submucosa or other ECM material when used in the present disclosure may also exhibit an angiogenic character and thus be effective to induce angiogenesis in a host engrafted with a device including the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g., human proteins applied to collagenous ECMs from other animals, such as pigs). The non-native bioactive components may also be drug substances. Illustrative drug substances that may be incorporated into and/or onto the ECM materials used in the present disclosure include, for example, antibiotics, thrombus-promoting substances such as blood clotting factors, e.g., thrombin, fibrinogen, and the like. These substances may be applied to the ECM material as a premanufactured step, immediately prior to the procedure (e.g., by soaking the material in a solution containing a suitable antibiotic such as cefazolin), or during or after engraftment of the material in the patient.

A non-native bioactive component can be applied to a collagenous extracellular matrix material by any suitable means. Suitable means include, for example, spraying, impregnating, dipping, etc. The non-native bioactive agent can be applied to the collagenous extracellular matrix material either before or after the material is affixed to an elongate member. Similarly, if other chemical or biological components are included in the collagenous extracellular matrix material, the non-native bioactive component can be applied either before, in conjunction with, or after these other components.

Submucosa or other ECM tissue used in the present disclosure is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present disclosure.

In additional embodiments, expandable member 38 or other first implant member, expander 34 or other second implant member, or anchor member 37 components in devices of the present disclosure can include ECMs or other collagenous materials that have been subjected to processes that expand the materials, such as described in U.S. patent application Ser. No. 12/489,199, published Dec. 31, 2009 as US 2009-0326577A1; Ser. No. 12/488,974, published Dec. 24, 2009 as US 2009-0318934A1 and Ser. No. 12/488,996, published Dec. 24, 2009 as US 2009-2009-3017469A1, as well as U.S. Provisional Patent Application No. 61/074,441. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e., 1.2 times) its original bulk volume, or in some forms to at least about two times its original volume. Thereafter, the expanded material can optionally be isolated from the alkaline medium, e.g., by neutralization and/or rinsing. The collected, expanded material can be used in any suitable manner in the preparation of a medical device. Illustratively, the expanded material can be enriched with bioactive components, formed into one or more layers, dried, and then associated with a body member.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECMs. Typically such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C.

for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g., 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g., about 100×. Consequently, an expanded collagenous material typically appears more porous than a corresponding non-expanded collagenous material. Moreover, in many instances, the expanded collagenous material can be demonstrated as having increased porosity, e.g., by measuring for an increased permeability to water or other fluid passage as compared to the non-treated starting material.

After such alkaline treatments, the material can be isolated from the alkaline medium and processed for further use. Illustratively, the collected material can be neutralized and/or rinsed with water to remove the alkalinity from the material, prior to further processing of the material. In certain forms, the treated material is comminuted to create a castable material such as a paste or dough, e.g., suspended in a liquid medium such as an aqueous medium. This castable material can be cast into molds, and then dried by lyophilization, air drying or otherwise, to form device components having sizes and configurations as disclosed herein, e.g., for the expandable member 38, expander 34 and/or anchor member 37.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc., as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded collagenous material.

In some embodiments, the anchor member 37 includes a frame comprising a single piece of superelastic wire or other material having a plurality of sides and bends interconnecting adjacent sides. The bends can be coils, fillets, or other configurations to reduce stress and fatigue. The single piece of wire is preferably joined by an attachment mechanism, such as a piece of cannula and solder, to form a closed circumference frame.

The frame of the anchor member 37 can comprise a metallic material including but not limited to stainless steel (e.g., 304 SS), titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, suitable frames can include material in the form of yarns, fibers, and/or resins, e.g., monofilament yarns, high tenacity polyester, and the like. A frame element can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon. Such metallic and other materials may be used in forming other expandable and non-expandable graft body components useful in the present disclosure. The anchor member 37 can also include a flexible material covering extending between sides of the frame. Such a covering can be formed with any suitable material discussed herein, such as but not limited to DACRON, PTFE, collagen, submucosa, or other flexible material, and can be attached to the frame with sutures or other suitable attachment means.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A device for providing hemostasis at a surgical site in a patient, where the surgical site includes a puncture in a vascular vessel and a tissue tract extending from the skin of the patient to the puncture, the device comprising:
    a delivery cannula having at least a portion advanceable into the tissue tract and through the puncture;
    an anchor member received in the delivery cannula, the anchor member configured to reside and anchor within the vascular vessel upon deployment from the delivery cannula and contact an inner surface of the vascular vessel;
    a tether connected to the anchor member, the tether configured to extend through the puncture and tissue tract when the anchor member is received within the vascular vessel;
    a first implant member for implantation in the tissue tract, the first implant member received in the delivery cannula proximal to the anchor member;
    a second implant member for implantation in the tissue tract, the second implant member received in the delivery cannula proximal to the anchor member, wherein the first and second implant members are sized and configured such that movement of at least a portion of the second implant member against the first implant member causes the first implant member to expand; and
    a pusher received in the delivery cannula for imparting a pushing force against the second implant member;
    wherein the first and second implant members are sized and configured such that said movement causes overlap of the first and second implant members with one another along a length of the device such that a portion of the first implant member and a portion of the second implant member co-extend along a length of the device.

2. The device of claim 1, wherein the first and second implant members are sized and configured such that said movement causes the first and second implant members to frictionally couple to one another.

3. The device of claim 1, wherein the first implant member defines a lumen and the second implant member defines at least a portion receivable within the lumen of the first implant member so as to expand the first implant member.

4. The device of claim 1, wherein at least a portion of the second implant member is received in the delivery cannula proximal to the first implant member.

5. The device of claim 1, wherein:
    the first implant member has a lumen extending at least partially along a length of the first implant member,
    the second implant member has at least a portion received outside of and movable into the lumen of the first implant member upon said movement; and
    the tether and pusher are so constructed and arranged that the tether can be tensioned to cause the anchor member to provide proximally-directed counterforce while the pusher is advanced distally to cause said movement.

6. The device of claim 1, wherein said first implant member comprises an extracellular matrix (ECM) material.

7. The device of claim 1, wherein at least one of said first implant member and second implant member is comprised of a bioabsorbable material.

8. The device of claim 1, wherein at least one of said first implant member and said second implant member is comprised of a sponge material.

9. The device of claim 1, wherein the second implant member has a tapered outer surface.

10. The device of claim 1, wherein the second implant member has a conically-shaped portion for receipt in a lumen of the first implant member.

11. The device of claim 1, wherein the second implant member is more resistant to compression than the first implant member.

12. The device of claim 11, wherein the second implant member is comprised of a synthetic biodegradable polymer and the first implant member is comprised of an extracellular matrix material.

13. The device of claim 1, wherein the first implant member defines a lumen extending from a proximal end to a distal end of the first implant member and the second implant member defines a lumen extending from a proximal end to a distal end of the second implant member.

14. The device of claim 13, wherein the tether extends through the lumen of the second implant member and the lumen of the first implant member.

15. The device of claim 1, wherein the pusher defines a lumen.

16. The device of claim 15, wherein the tether extends through the lumen of the pusher.

17. The device of claim 1, wherein the first implant member has a generally cylindrical body having a longitudinal lumen extending at least partially along a length of the generally cylindrical body, and the second implant member has at least a conically-shaped portion for receipt in a lumen of the first implant member upon said movement.

18. A device for providing hemostasis at a surgical site in a patient, where the surgical site includes a puncture in a vascular vessel and a tissue tract extending from the skin of the patient to the puncture, the device comprising:
    a first implant member sized for receipt in the tissue tract, the first implant member having a proximal end and a distal end;
    a second implant member sized for receipt in the tissue tract, the second implant member having a proximal end and a distal end, wherein the first and second implant members are sized and configured such that movement of at least a portion of the second implant member against the first implant member causes frictional coupling of the first and second implant members and urges the first implant member to expand; and at least one force-transmitting member for causing said movement;

wherein said at least one force transmitting member includes an anchor member residing distal of the distal end of the first implant member and a tether connected to the anchor member, the anchor member and tether arranged to apply proximally-directed force to the first implant member; wherein the first and second implant members are sized and configured such that said movement causes overlap of the first and second implant members with one another along a length of the device such that a portion of the first implant member and a portion of the second implant member co-extend along a length of the device.

19. The device of claim 18, wherein said at least one force transmitting member includes a pusher arranged to apply distally-directed force to the second implant member.

* * * * *